US012788428B2

(12) United States Patent
Tada et al.

(10) Patent No.: US 12,788,428 B2
(45) Date of Patent: Nov. 10, 2026

(54) MEDICAL SYSTEM

(71) Applicant: TERUMO KABUSHIKI KAISHA, Tokyo (JP)

(72) Inventors: Yuichi Tada, Santa Clara, CA (US); Yoichiro Kuwano, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 707 days.

(21) Appl. No.: 18/177,634

(22) Filed: Mar. 2, 2023

(65) Prior Publication Data

US 2023/0277211 A1 Sep. 7, 2023

(30) Foreign Application Priority Data

Mar. 4, 2022 (JP) ................................ 2022-033303

(51) Int. Cl.
*A61B 17/3207* (2006.01)
*A61B 17/00* (2006.01)

(52) U.S. Cl.
CPC ................ *A61B 17/320758* (2013.01); *A61B 2017/00022* (2013.01); *A61B 2217/005* (2013.01)

(58) Field of Classification Search
CPC .... A61B 17/32058; A61B 2017/00022; A61B 2017/00115; A61B 2017/22039; A61B 2217/005; A61B 2090/064
See application file for complete search history.

(56) References Cited

U.S. PATENT DOCUMENTS

| | | | | |
|---|---|---|---|---|
| 4,935,005 | A * | 6/1990 | Haines | A61M 1/742 604/35 |
| 9,956,040 | B1 * | 5/2018 | Lastarria | A61B 18/22 |
| 10,702,299 | B2 | 7/2020 | Barak et al. | |
| 2006/0084961 | A1 * | 4/2006 | Kadziauskas | A61F 9/008 606/4 |
| 2015/0105791 | A1 * | 4/2015 | Truckai | A61B 17/00234 606/115 |

FOREIGN PATENT DOCUMENTS

| | | |
|---|---|---|
| JP | 2017-521153 A | 8/2017 |

* cited by examiner

*Primary Examiner* — Anh T Dang
(74) *Attorney, Agent, or Firm* — Kim & Stewart LLP

(57) ABSTRACT

A medical system includes a device for removing an object in a body cavity, the device including a shaft portion including a rotatable drive shaft and a lumen, a motor configured to rotate the drive shaft, a cutter attached to a distal end of the drive shaft and configured to cut the object when the drive shaft is rotated by the motor, and a pump operable according to one or more parameters to create a vacuum in the lumen to transport the cut object through the lumen. The system further includes one or more sensors each configured to detect a physical quantity related to the cut object transported through the lumen, and a controller configured to determine the parameters based on the physical quantity detected by each of the sensors, and control the pump to create the vacuum in the lumen according to the determined parameters.

12 Claims, 5 Drawing Sheets

MEDICAL SYSTEM

CROSS-REFERENCE TO RELATED APPLICATION(S)

This application is based on and claims the benefit of priority from Japanese patent application No. 2022-033303, filed Mar. 4, 2022, the entire contents of which are incorporated herein by reference.

BACKGROUND

Technical Field

Embodiments described herein relate generally to a medical system, a controller for a medical system, and a method carried out by a medical system.

Related Art

In recent years, medical devices for cutting a thrombus or the like from a biological body cavity such as a blood vessel have been used. Such medical devices include an atherectomy device including a cutting unit for cutting a lesion such as plaque or a thrombus in the blood vessel. The cut object is sucked to the outside through the inside of the atherectomy device.

SUMMARY

The suction force acting on the atherectomy device or the like is desirably adjusted optimally depending on the progress of the medical operation. However, it is difficult to adjust the suction force according to the changing conditions inside the body cavity. For example, in a case where a cut piece is stuck in the atherectomy device, the suction force of the atherectomy device is preferably adjusted to increase. However, it is difficult to determine how to adjust suction parameters such as the suction force according to the changing situation, and it is difficult to appropriately operate the suction unit that applies the suction force.

Embodiments of the present invention provide a control device for a medical system, a medical system, and a control method for a medical system, in which suction of the cut piece of the object in the blood vessel is appropriately and automatically performed according to the situation inside a body cavity.

In one embodiment, a medical system includes a device for removing an object in a body cavity, the device including a shaft portion including a rotatable drive shaft and a lumen, a motor configured to rotate the drive shaft, a cutter attached to a distal end of the drive shaft and configured to cut the object when the drive shaft is rotated by the motor, and a pump operable according to one or more parameters to create a vacuum in the lumen to transport the cut object through the lumen. The system further includes one or more sensors each configured to detect a physical quantity related to the cut object transported through the lumen, and a controller configured to determine the parameters based on the physical quantity detected by each of the sensors, and control the pump to create the vacuum in the lumen according to the determined parameters.

In another embodiment, a controller controls a medical system including a device for removing an object in a body cavity, the device including a shaft portion including a rotatable drive shaft and a lumen, a motor configured to rotate the drive shaft, a cutter attached to a distal end of the drive shaft and configured to cut the object when the drive shaft is rotated by the motor, and a pump operable according to one or more parameters to create a vacuum in the lumen to transport the cut object through the lumen, and one or more sensors each configured to detect a physical quantity related to the cut object transported through the lumen. The controller comprises a memory and a processor configured to determine the parameters based on the physical quantity detected by each of the sensors, and control the pump to create the vacuum in the lumen according to the determined parameters.

In yet another embodiment, a method is carried out by a medical system that includes a device for removing an object in a body cavity, the device including a shaft portion including a rotatable drive shaft and a lumen, a motor configured to rotate the drive shaft, a cutter attached to a distal end of the drive shaft and configured to cut the object when the drive shaft is rotated by the motor, and a pump operable according to one or more parameters to create a vacuum in the lumen to transport the cut object through the lumen, and one or more sensors each configured to detect a physical quantity related to the cut object transported through the lumen. The method comprises determining the parameters based on the physical quantity detected by each of the sensors, and controlling the pump to create the vacuum in the lumen according to the determined parameters.

In the medical system, the controller, and the method as described above, the operation of the pump can be controlled according to the detected physical quantity, and thus suction of the cut piece of the object in the blood vessel is appropriately and automatically performed according to the situation.

DETAILED DESCRIPTION

Figure 1:
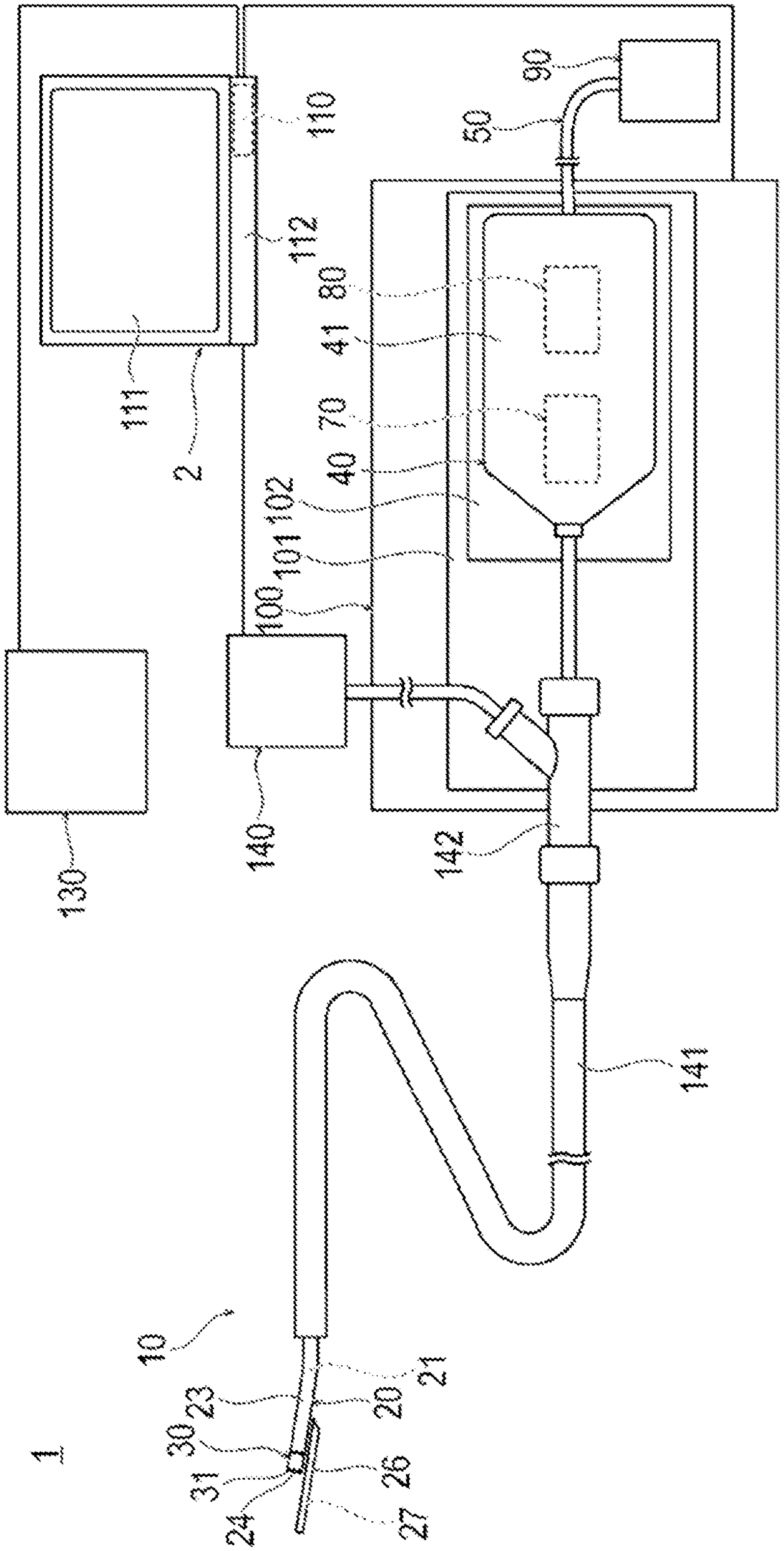
FIG. 1 is an overall front view of a medical system according to a first embodiment.

Hereinafter, embodiments of the present invention will be described with reference to the drawings. The size and ratio of each member in the drawings may be exaggerated for illustration and may be different from the actual size and ratio.

First Embodiment

A medical system 1 according to the first embodiment includes a medical device 10 that is inserted into a blood vessel, and is used for a treatment to destroy and discharge a lesion such as thrombus, plaque, an atheroma, or a calcified lesion (hereinafter also referred to as an object) in an acute lower limb ischemia or a deep vein thrombosis. In the present specification, a side of the medical device 10 to be inserted into the blood vessel is referred to as a "distal side", and a side of the medical device 10 to be operated by the operator is referred to as a "proximal side". The object to be destroyed and discharged is not necessarily limited to the thrombus, the plaque, the atheroma, and the calcified lesion, and may be any object that can exist in the biological body cavity.

Figure 2:
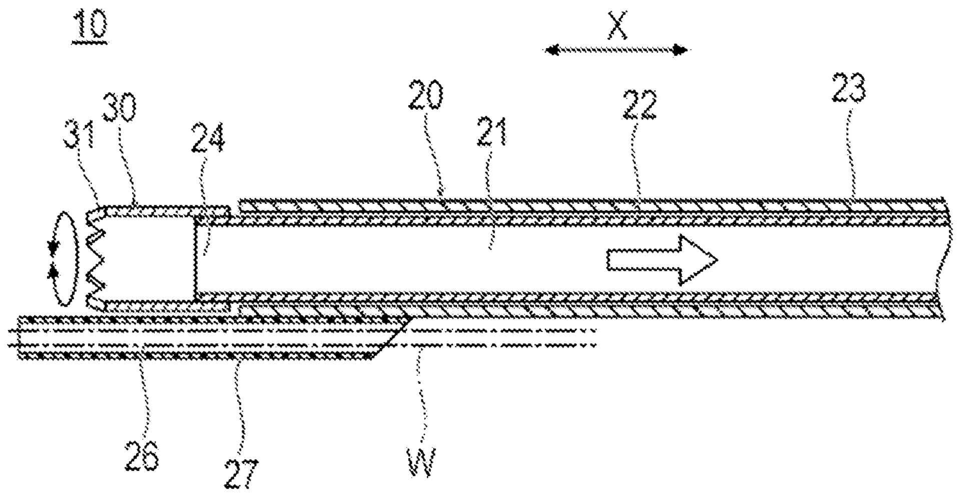
FIG. 2 is an enlarged cross-sectional view of a distal end portion of a medical device according to the first embodiment.
Figure 3:
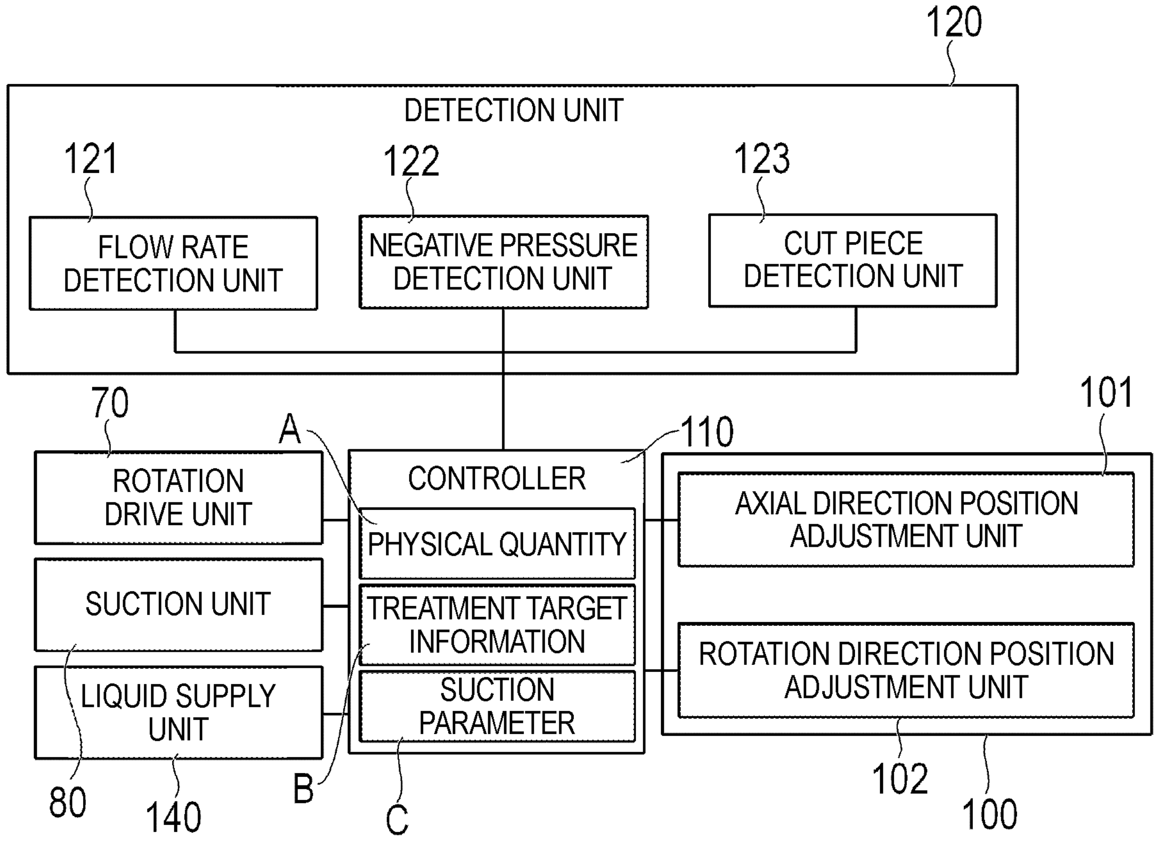
FIG. 3 is a hardware block diagram of the medical system according to the first embodiment.

As illustrated in FIGS. 1 to 3, the medical device 10 of the medical system 1 includes a cutting unit 30 disposed at a distal end portion for destroying the object, a position adjustment unit 100 that adjusts a position of the medical device 10 in the body cavity, a liquid supply unit 140 that supplies a liquid to the medical device 10, a control device 2 including a controller 110 that controls operation of the medical device 10 and operation of the position adjustment unit 100, and operation of the liquid supply unit 140, and a detection unit 120 that is positioned near the medical device 10 during a medical operation and detect various physical quantities (e.g., a suction flow rate) related to the suction operation of the medical system 1. The details of the physical quantities are described later.

The medical device 10 includes a long shaft portion 20 having a discharge lumen 21 through which an object can be carried to the proximal side, a cutting unit 30 disposed at a distal end portion of the shaft portion 20, and an operation unit 40 to which the proximal end portion of the shaft portion 20 is connected. The medical device 10 further includes a rotation drive unit 70 that rotates a drive shaft 22 provided in the shaft portion 20, a suction unit 80 that communicates with the discharge lumen 21 provided in the shaft portion 20, a discharge passage 50 through which a waste liquid sucked by the suction unit 80 is discharged, and a waste liquid bag 90 that communicates with the discharge passage 50 and receives the waste liquid through the discharge passage 50.

The shaft portion 20 includes the drive shaft 22 rotationally driven by the rotation drive unit 70, an outer tube 23 that rotatably accommodates the drive shaft 22, and a distal end tube 26 fixed to a side surface of a distal end portion of the outer tube 23.

The drive shaft 22 is connected to the cutting unit 30 and transmits rotational force to the cutting unit 30. The drive shaft 22 is flexible and capable of transmitting rotational power acting from the proximal side to the distal side. The drive shaft 22 has the discharge lumen 21 formed for moving the cut object to the proximal side. The drive shaft 22 penetrates the outer tube 23, and has the cutting unit 30 fixed to the distal end portion of the drive shaft 22. The proximal end portion of the drive shaft 22 is connected to the rotation drive unit 70. The drive shaft 22 has a distal end opening 24 at the distal end at which the discharge lumen 21 is open. The distal end opening 24 is an inlet which the cut piece, which is a suction target formed when being cut, enters. The proximal end portion of the drive shaft 22 is connected to the suction unit 80 that applies suction force to the discharge lumen 21. The discharge lumen 21 may be formed not inside the drive shaft 22 but between the outer tube 23 and the drive shaft 22 or inside another tube provided inside the drive shaft 22.

The cutting unit 30 is a cutter that cuts an object such as a thrombus, plaque, or a calcified lesion to make the object small. Therefore, "cutting an object" means contacting an object and applying force to the object so as to make the object small. The method of applying a force in cutting operation and the shape and form of the cut object are not limited. The cutting unit 30 has strength with which the above-described object can be cut. The cutting unit 30 is fixed to the distal end portion of the drive shaft 22. The cutting unit 30 includes a cylinder protruding toward the distal side of the drive shaft 22. The cutting unit 30 may be hollow and in communication with the discharge lumen 21. The distal end of the cutting unit 30 includes a sharp blade. The shape of the blade is not particularly limited. The cutting unit 30 may have a large number of fine abrasive grains instead of the blade.

The rotation drive unit 70 is disposed inside the operation unit 40 and rotates the drive shaft 22. The rotation drive unit 70 is, for example, a motor. The rotational speed of the rotation drive unit 70 is not particularly limited, and ranges from 5,000 rpm to 200,000 rpm, for example.

The suction unit 80 is disposed inside operation unit 40. The suction unit 80 is, for example, a pump, and communicates with the proximal end portion of the discharge lumen 21 of the drive shaft 22 to apply suction force (i.e., negative pressure) to the discharge lumen 21. The suction unit 80 moves the waste liquid sucked through the discharge lumen 21 to the downstream side and discharges the waste liquid to the waste liquid bag 90. The suction unit 80 is, for example, a peristaltic pump, but may be a diaphragm pump. The peristaltic pump partially squeezes a tube containing the waste liquid with a plurality of rotating rollers, and moves a squeezing position to move the fluid inside the tube.

The outer tube 23 is a tube body having flexibility, and rotatably accommodates the drive shaft 22. The proximal end portion of the outer tube 23 is fixed to the operation unit 40. The outer tube 23 may have a bending portion that bends at a predetermined angle at a distal end portion thereof. Therefore, by rotating the outer tube 23, it is possible to change the orientation of the distal end portion of the outer tube 23 and easily bring the cutting unit 30 into contact with the object to be removed.

The distal end tube 26 is a tubular body having flexibility, and is fixed to the outer circumference surface of the distal end portion of the outer tube 23. The distal end tube 26 has a guide wire lumen 27 into which a guide wire can be inserted. When the outer tube 23 rotates, the position of the distal end tube 26 in the rotation direction of the outer tube 23 changes.

The discharge passage 50 is disposed between the suction unit 80 and the waste liquid bag 90, and conveys the waste liquid discharged from the suction unit 80 to the waste liquid bag 90. The discharge passage 50 is preferably transparent or translucent such that the operator can visually observe the internal flow.

The position adjustment unit 100 includes an axial direction position adjustment unit 101 that moves the shaft portion 20 in its axial direction X, and a rotation direction position adjustment unit 102 that rotates the shaft portion 20 about the axial direction X.

The axial direction position adjustment unit 101 is connected to the operation unit 40 and/or the shaft portion 20 of the medical device 10, and has a linear movement drive mechanism that linearly moves the operation unit 40 and/or the shaft portion 20 in the axial direction X. The linear movement drive mechanism may include a roller that rotates to move the shaft portion 20 in contact with the outer circumference surface thereof. The operation of the linear movement drive mechanism is controlled by the controller 110. Therefore, the axial direction position adjustment unit 101 can move the shaft portion 20 and the cutting unit 30 in the axial direction X according to instructions or control signals issued by the controller 110.

The rotation direction position adjustment unit 102 is connected to the operation unit 40 and/or the shaft portion 20 of the medical device 10, and has a rotation drive mechanism that rotates the operation unit 40 and/or the shaft portion 20 about the axial direction X. The operation of the rotation drive mechanism is controlled by the controller 110. Therefore, the rotation direction position adjustment unit 102 can rotate the shaft portion 20 about the axial direction X according to instructions or control signals issued by the controller 110. The position adjustment unit 100 including the axial direction position adjustment unit 101 and the rotation direction position adjustment unit 102 may be a three-dimensionally operable robot arm or the like.

The liquid supply unit 140 supplies a liquid such as physiological saline to the vicinity of the cutting unit 30 in the blood vessel. The liquid supply unit 140 is, for example, a pump. For example, the liquid supply unit 140 can supply a liquid to a sheath 141 into which the shaft portion 20 is inserted via a Y connector 142. The liquid supply unit 140 is, for example, a peristaltic pump, but may be a diaphragm pump. In the present embodiment, the liquid supply unit 140 is an external device of the medical device 10, but may be a part of the medical device 10. For example, the liquid supply unit 140 may be disposed inside the operation unit 40 and supply the liquid into the blood vessel through a lumen (for example, a gap between the drive shaft 22 and the outer tube 23) other than the discharge lumen 21 of the shaft portion 20. The operation of the liquid supply unit 140 is controlled by the controller 110.

The controller 110 includes a storage circuit and an arithmetic circuit. The storage circuit is, for example, a memory, and can store programs and various parameters. The arithmetic circuit is, for example, a processor such as a central processing unit (CPU), and can read programs and various parameters from the storage circuit to perform arithmetic processing.

The controller 110 controls a display unit 111 such as a monitor that displays information as an image and an input unit 112 such as a touch panel, a keyboard, and/or a mouse such that the operator can perform operations and various settings.

The controller 110 controls the operation of each of the rotation drive unit 70, the suction unit 80, the liquid supply unit 140, the axial direction position adjustment unit 101, and the rotation direction position adjustment unit 102. The controller 110 calculates one or more suction parameters C on the basis of one or more physical quantities A related to suction operation of the medical system 1, and treatment target information B acquired in advance, and controls the operation of the medical system 1 according to the calculated suction parameters C.

The physical quantities A related to the suction operation include a suction flow rate FL generated by suction, a negative pressure amount P generated by suction, a temporal change in relationship between the suction flow rate and the negative pressure amount, and properties of cut objects, e.g., the quantity and/or the total volume thereof, the size and/or the hardness of the cut object, and the like. The size of the cut object is a representative size of at least one cut object (for example, an average value, a maximum value, a minimum value, and the like). The hardness of the cut object is a representative hardness of at least one cut object (for example, an average value, a maximum value, a minimum value, and the like).

A flow rate detection unit 121 that detects the suction flow rate FL generated by suction is, for example, a gravimeter that detects the weight of the waste liquid bag 90. The flow rate detection unit 121 is an imaging device (e.g., a camera) that is disposed at a position at which the insides of the discharge passage 50 and the waste liquid bag 90 can be imaged from the outside. In this case, the controller 110 can detect the suction flow rate FL from the image obtained by the imaging device by a known image recognition technology. The suction flow rate FL may be detected by a flow meter disposed in the discharge passage 50, the discharge lumen 21, or the suction unit 80.

A negative pressure detection unit 122 that detects the negative pressure amount P generated by suction is, for example, a pressure gauge that is disposed at any position of the discharge lumen 21. The negative pressure detection unit 122 may be disposed in the suction unit 80. The negative pressure amount P is an amount of pressure decreased from the atmospheric pressure or blood pressure, and the negative pressure amount P increases as the pressure decreases. A plurality of negative pressure detection units 122 may be disposed at various locations. For example, the negative pressure detection units 122 may be disposed in the vicinity of the distal end of the discharge lumen 21 and the suction unit 80.

A cut piece detection unit 123 that detects the properties of cut objects (e.g., the amount of cut objects, the size of the cut object, the hardness of the cut object, and the like) is, for example, an imaging device (e.g., a camera). The cut piece detection unit 123 may be disposed at a position at which the inside of the discharge passage 50 or the inside of the waste liquid bag 90 can be imaged from the outside. The flow rate detection unit 121 and the cut piece detection unit 123 may be configured by the same imaging device.

The treatment target information B acquired in advance is, for example, the shape of a blood vessel or the shape of a lesion, the hardness of the lesion, or the like. The shape of the blood vessel or the shape of the lesion is detected by a known image recognition technology with a two-dimensional or three-dimensional image detected by, for example, intravascular ultrasound (IVUS), optical coherence tomography (OCT), imaging with a camera, ultrasonic diagnostic imaging, computed tomography (CT), magnetic resonance imaging (MRI), or the like.

The suction parameters C include suction force of the suction unit 80, and a suction time for continuing suction operation of the suction unit 80. The suction force of the suction unit 80 can be defined by the flow rate and pressure of the pump constituting the suction unit 80. It may be defined by a current, a voltage, power, or the like supplied to a drive source such as a motor that drives a pump constituting the suction unit 80. At least one of the suction parameters C may be one of the above-described physical quantities A related to suction operation of the medical system 1.

The controller 110 calculates, determines, or selects desirable suction parameters C based on the physical quantities A acquired during the operation of the medical device 10 and the treatment target information B acquired in advance. For example, in a case where it is determined that a lumen of the medical device 10 such as the discharge lumen 21 or the discharge passage 50 is clogged with a cut object or in a case where it is determined that the amount, size, hardness, or the like of the cut object to be sucked is increased from the change in the physical quantities A, the controller 110 can calculate and change the desirable suction parameters C in order to increase the suction force or increase the suction time.

The change in the physical quantities A with which it can be determined that a lumen of the medical device 10 is clogged with a cut objects can be specified, for example, from a relationship between the suction flow rate FL detected by the flow rate detection unit 121 and the negative pressure amount P detected by the negative pressure detection unit 122. When the medical device 10 is clogged with the cut object, the suction flow rate FL decreases. When the lumen of the medical device 10 is clogged with the cut object, in a case where the negative pressure detection unit 122 is at a position separated from the suction unit 80 other than a position clogged with the cut object, the negative pressure hardly acts on the negative pressure detection unit 122, and thus the negative pressure amount P decreases. When the lumen of the medical device 10 is clogged with the cut object, in a case where the negative pressure detection unit 122 is at a position close to the suction unit 80 other than a position clogged with the cut object, the negative pressure strongly acts on the negative pressure detection unit 122, and thus the negative pressure amount P increases. Therefore, the controller 110 can determine that the cut object is stuck by monitoring a change in suction flow rate FL and/or negative pressure amount P, which are the physical quantities A. The controller 110 can determine that the cut object is stuck and can also specify the clogged position to some extent by monitoring the change in relationship between the suction flow rate FL and the negative pressure amount P, which are the physical quantities A.

For example, in a case where the controller 110 determines that the amount, size, or hardness of the cut object to be sucked decreases from the change in the physical quantities A, the suction parameters C can be changed in order to decrease the suction force or decrease the suction time.

An example of the change in the physical quantities A with which it be determined that the amount, size, or hardness of the cut object to be sucked decreases includes a decrease in the amount, size, or hardness of the cut object in the discharge passage 50 or the waste liquid bag 90 detected by the cut piece detection unit 123.

In a case where it is determined that a stop condition for stopping cutting operation by the cutting unit 30 is satisfied on the basis of the change in the physical quantities A, the controller 110 can stop the rotation drive unit 70 to stop the cutting operation. The stop condition may be, for example, whether the amount of the cut object detected by the cut piece detection unit 123 exceeds a threshold. In this case, in a case where a new cut object is not detected by the cut piece detection unit 123, the controller 110 can determine that the cutting operation is completed and stop the rotation drive unit 70.

The controller 110 can stop the suction unit 80 after stopping the rotation drive unit 70.

Figure 4:
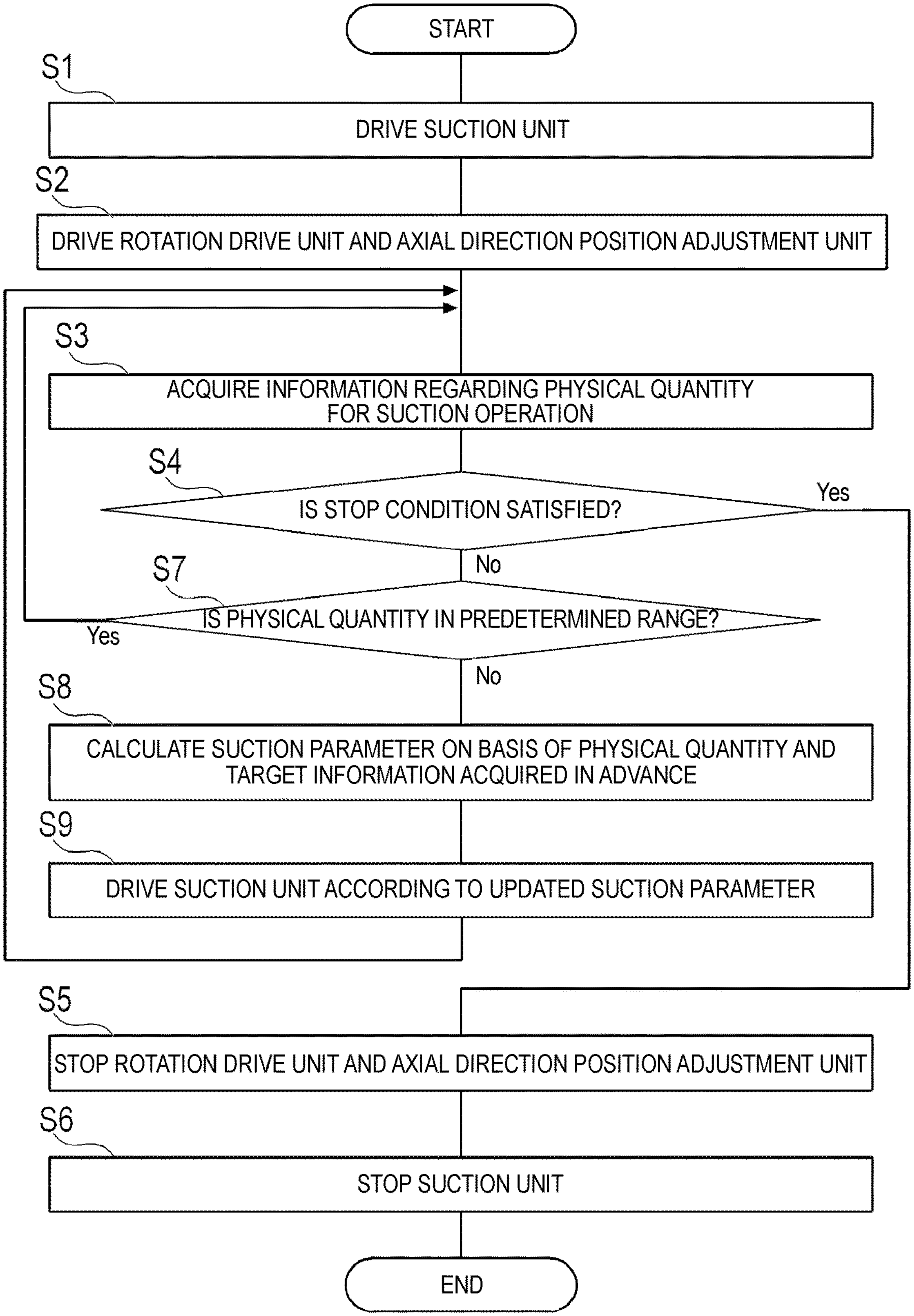
FIG. 4 is a flowchart illustrating operation of a controller according to the first embodiment.

Next, the operation control for the medical system 1 will be described with reference to a flowchart illustrated in FIG. 4.

Before performing a treatment for a patient using the medical system 1, the controller 110 stores treatment target information B of the patient. The treatment target information B acquired in advance includes, for example, a three-dimensional or two-dimensional image of a blood vessel and a lesion L to be removed, the hardness of the lesion L that can be specified from the image, or the like.

Figure 5:
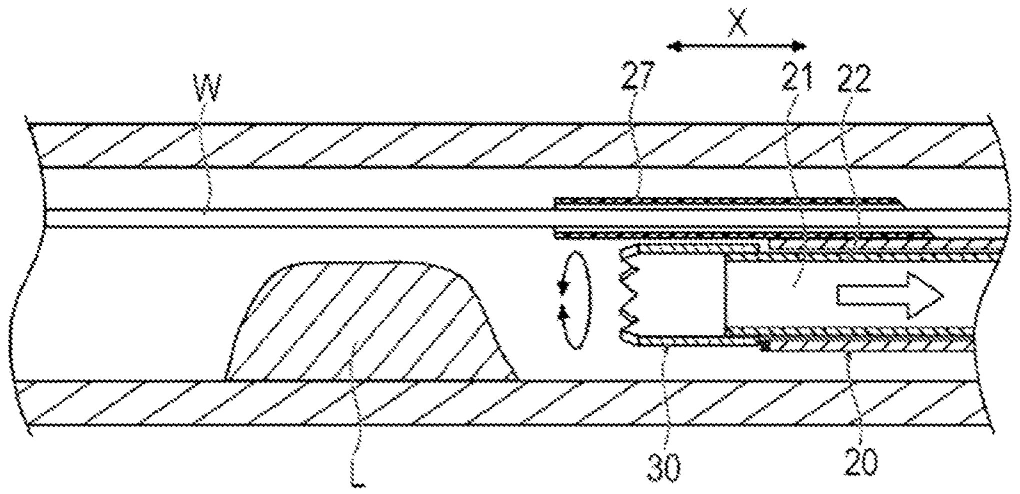
FIG. 5 is a cross-sectional view of the medical device with a cutting unit positioned near a lesion.

Next, an operator inserts the proximal end of a guide wire W into the guide wire lumen 27 of the medical device 10. Next, as illustrated in FIG. 5, the operator inserts the medical device 10 into the blood vessel by using the guide wire W as a guide. Thereafter, the operator moves the shaft portion 20 in the distal direction using the axial direction position adjustment unit 101 or manually until the cutting unit 30 reaches the vicinity of the lesion L.

Next, the operator operates the controller 110 to start control by the controller 110. The controller 110 drives the suction unit 80 under initially set suction parameters C (S1). According to this, suction force acts on the discharge lumen 21. Subsequently, the controller 110 causes the axial direction position adjustment unit 101 to move the cutting unit 30 in the axial direction X while causing the rotation drive unit 70 to rotate the cutting unit 30 at a predetermined rotational speed (S2).

Next, the controller 110 acquires information regarding the physical quantities A related to suction operation (S3). Specifically, the controller 110 receives a signal indicating the physical quantity A from at least one of the flow rate detection unit 121, the negative pressure detection unit 122, and the cut piece detection unit 123.

When determining that the change in the acquired physical quantity A satisfies the preset stop condition (S4), the controller 110 stops the rotation drive unit 70 to stop the rotation of the cutting unit 30, and causes the axial direction position adjustment unit 101 to stop the movement of the cutting unit 30 (S5).

Subsequently, the controller 110 stops the suction unit 80 to stop suction (S6). Since the suction unit 80 is stopped after the rotation of the cutting unit 30 by the suction unit 80 is stopped, it is possible to prevent the cut object from remaining in the blood vessel. Therefore, the operation control for the medical system 1 by the controller 110 is completed. The controller 110 can also control the axial direction position adjustment unit 101 to stop the suction unit 80 and then automatically remove the medical device 10 from the blood vessel.

When determining that the acquired physical quantity A does not satisfy the stop condition (S4), the controller 110 determines whether or not the acquired physical quantity A is within a predetermined range (S7).

When determining that the physical quantity A related to suction operation is within a predetermined range set in advance (S7), the controller 110 causes processing to return to processing of S3 while continuing the suction operation and the cutting operation without changing the suction parameters C, and acquires information regarding the physical quantity A related to suction operation again (S3).

When determining that the physical quantity A related to suction operation is not within the predetermined range (S7), the controller 110 calculates and updates the suction parameters C on the basis of the physical quantity A related to suction operation and treatment target information B acquired in advance (S8). Next, the controller 110 controls the operation of the suction unit 80 according to the updated new suction parameters C (S9). Subsequently, the controller 110 caused processing to return to S3, and acquires information regarding the physical quantity A related to suction operation again (S3). Thereafter, the controller 110 repeatedly executes steps of S3 to S4 and steps of S7 to S9 until the stop condition of S4 is satisfied.

As described above, according to the first embodiment, there is provided the control device 2 for the medical system 1 configured to cut an object in a blood vessel, the medical system 1 including: the long shaft portion 20; the cutting unit 30 provided at a distal end portion of the shaft portion 20; the rotation drive unit 70 and/or the position adjustment unit 100 configured to operate the cutting unit 30; the suction unit 80 configured to apply suction force; and the detection unit 120 configured to detect at least one physical quantity A related to suction operation of the medical system 1, the control device 2 including the controller 110 configured to control the operation of the suction unit 80, in which the controller 110 is capable of calculating at least one suction parameter C on the basis of at least one physical quantity A, and controls the suction unit 80 on the basis of at least one suction parameter C.

According to the first embodiment, there is provided the control device 2 for the medical system 1 configured to cut an object in a blood vessel, the control device 2 including the long shaft portion 20, the cutting unit 30 provided at a distal end portion of the shaft portion 20, the rotation drive unit 70 and/or the position adjustment unit 100 configured to operate the cutting unit 30, the suction unit 80 configured to apply suction force, the detection unit 120 configured to detect at least one physical quantity A related to suction operation of the medical system 1, and the controller 110 configured to control the operation of the suction unit 80, in which the controller 110 is capable of calculating at least one suction parameter C on the basis of at least one physical quantity A, and controls the suction unit 80 on the basis of at least one suction parameter C.

In the control device 2 for the medical system 1 as described above, the operation of the suction unit 80 is controlled according to the detected physical quantity A, and thus suction of a cut piece of the object in the blood vessel, which is cut by the cutting unit 30, is appropriately and automatically performed according to the situation. Therefore, it is possible to effectively prevent the medical device 10 from being clogged with the cut object, and effectively prevent the suction force from unintentionally decreasing.

The suction parameter C indicates at least one of suction force of the suction unit 80 or a suction time for continuing suction operation of the suction unit 80. Therefore, the control device 2 for the medical system 1 can automatically perform appropriate suction operation by controlling the suction operation of the suction unit 80 according to the detected physical quantity A, and thus the workability can be improved.

At least one physical quantity A related to suction operation includes at least one of a suction flow rate FL generated by the suction unit 80, a negative pressure amount P generated by the suction unit 80, a relationship between the suction flow rate FL and the negative pressure amount P, an amount of a cut piece of an object cut by the cutting unit 30, a size of the cut piece of the object, or a hardness of the cut piece of the object. Therefore, the control device 2 for the medical system 1 can control the operation of the suction unit 80 according to the physical quantity A sensitively changed according to the situation, and automatically perform appropriate suction operation.

At least one physical quantity A for suction operation includes the suction flow rate FL generated by the suction unit 80, the suction parameter C includes the suction force of the suction unit 80, and the controller 110 increases the suction force of the suction unit 80 in a case where the suction flow rate FL is less than a preset threshold. Therefore, the control device 2 determines that a lumen of the medical device 10 such as the discharge lumen 21 or the discharge passage 50 is clogged with the cut piece of the object from the change in suction flow rate FL which is the physical quantity A, and can remove the clogging with the cut piece by increasing the suction force of the suction unit 80.

At least one physical quantity A for suction operation includes the negative pressure amount P generated by the suction unit 80, the suction parameter C includes the suction force of the suction unit 80, and the controller 110 increases the suction force of the suction unit 80 in a case where the negative pressure amount P changes more than a threshold for the negative pressure amount P set in advance. Therefore, the control device 2 determines that a lumen of the medical device 10 such as the discharge lumen 21 or the discharge passage 50 is clogged with the cut piece from the change in negative pressure amount P which is the physical quantity A, and can remove the clogging with the cut piece of the object by increasing the suction force of the suction unit 80. Whether the negative pressure amount P increases or decreases when the medical device 10 is clogged with the cut piece varies depending on a relationship among a position of the suction unit 80, a position clogged with the cut piece, and a position of the negative pressure detection unit 122. For example, in a case where the negative pressure detection unit 122 is at a position separated from the suction unit 80 other than a position clogged with the cut piece, the negative pressure hardly acts on the negative pressure detection unit 122, and thus the negative pressure amount P decreases. In a case where the negative pressure detection unit 122 is at a position close to the suction unit 80 other than a position clogged with the cut piece, the negative pressure strongly acts on the negative pressure detection unit 122, and thus the negative pressure amount P increases. Therefore, it is preferable to appropriately set a threshold of the negative pressure amount P for determining that the medical device 10 is clogged with the cut piece according to a position at which the negative pressure detection unit 122 is disposed. For example, in a case where the negative pressure detection unit 122 is in the vicinity of the distal end of the discharge lumen 21, when the discharge lumen 21 is clogged with the cut piece, it is considered that the negative pressure detection unit 122 is always at a position separated from the suction unit 80 other than the position at which the discharge lumen 21 is clogged with the cut piece, and thus the negative pressure amount P decreases. Therefore, the threshold of the negative pressure amount P for determining that the medical device 10 is clogged with the cut piece is preferably set to a value with which a decrease in negative pressure amount P can be detected. A plurality of negative pressure detection units 122 may be disposed at different positions. For example, the negative pressure detection units 122 may be disposed in the vicinity of the distal end of the discharge lumen 21 and the suction unit 80. Therefore, for example, in a case where the negative pressure amount P detected in the vicinity of the distal end of the discharge lumen 21 decreases below a first threshold and the negative pressure amount P detected in the suction unit 80 increases above a second threshold, the control device 2 can determine that the cut piece is stuck between the distal end of the discharge lumen 21 and the suction unit 80. The first threshold and the second threshold are values different from each other, and the second threshold is greater than the first threshold.

After increasing the suction force of the suction unit 80 in accordance with the change in suction flow rate FL or negative pressure amount P, which is the physical quantity A, the controller 110 may stop suction operation of the suction unit 80 in a case where a state in which the suction flow rate FL or the negative pressure amount P is changed continues over a predetermined time. Therefore, the controller 110 can determine that the clogging with the cut piece cannot be removed by increasing the suction force of the suction unit 80 and maintaining a state in which the suction force is increased, and can stop the suction operation.

At least one physical quantity A for suction operation includes the size of the cut piece, and in a case where the size of the cut piece exceeds a preset reference value, the controller 110 may continue the suction operation of the suction unit 80 without stopping the suction operation in a case where a state in which the suction flow rate FL or the negative pressure amount P is changed continues over a predetermined time. When the cut piece is large, the flow passage such as the discharge lumen 21 or the discharge passage 50 may be clogged in a short time. However, when the cut piece is stuck only in a short time, there is a possibility that clogging of the large cut piece can be removed by increasing the suction force. Therefore, in a case where the cut piece is large, the controller 110 can control the suction unit 80 such that the emergency stop of suction operation of the suction unit 80 does not work only when the flow passage such as the discharge lumen 21 or the discharge passage 50 is clogged in a short time.

The controller 110 determines whether or not at least one of the physical quantities A detected by the detection unit 120 is within a predetermined range, does not change the suction parameter C in a case where the physical quantity A is within the predetermined range, and calculates and updates the suction parameter C on the basis of the physical quantity A in a case where the physical quantity A exceeds the predetermined range. Therefore, the control device 2 for the medical system 1 does not change the suction parameter C until it is necessary to change the suction parameter C, and when it is necessary to change the suction parameter C, the suction parameter C is automatically and appropriately changed, and thus the cut piece can be always cut under an appropriate condition.

Before stopping the suction unit 80, the controller 110 controls the rotation drive unit 70 to stop the cutting operation of the cutting unit 30. Therefore, the suction unit 80 can prevent the cut piece formed by the cutting unit 30 from remaining in the blood vessel.

The controller 110 may determine whether or not at least one of the physical quantities A detected by the detection unit 120 is within a predetermined range, and causes the liquid supply unit 140 that supplies a liquid to operate in a case where the physical quantity A exceeds the predetermined range. In this configuration, for example, physiological saline supplied from the liquid supply unit 140 is released to the vicinity of the cutting unit 30 through the Y connector 142 and the sheath 141. Therefore, the cut piece and blood sucked from the distal end opening 24 to the discharge lumen 21 is diluted with the physiological saline, and thus it is possible to effectively suppress clogging of the medical device 10.

Second Embodiment

Figure 6:
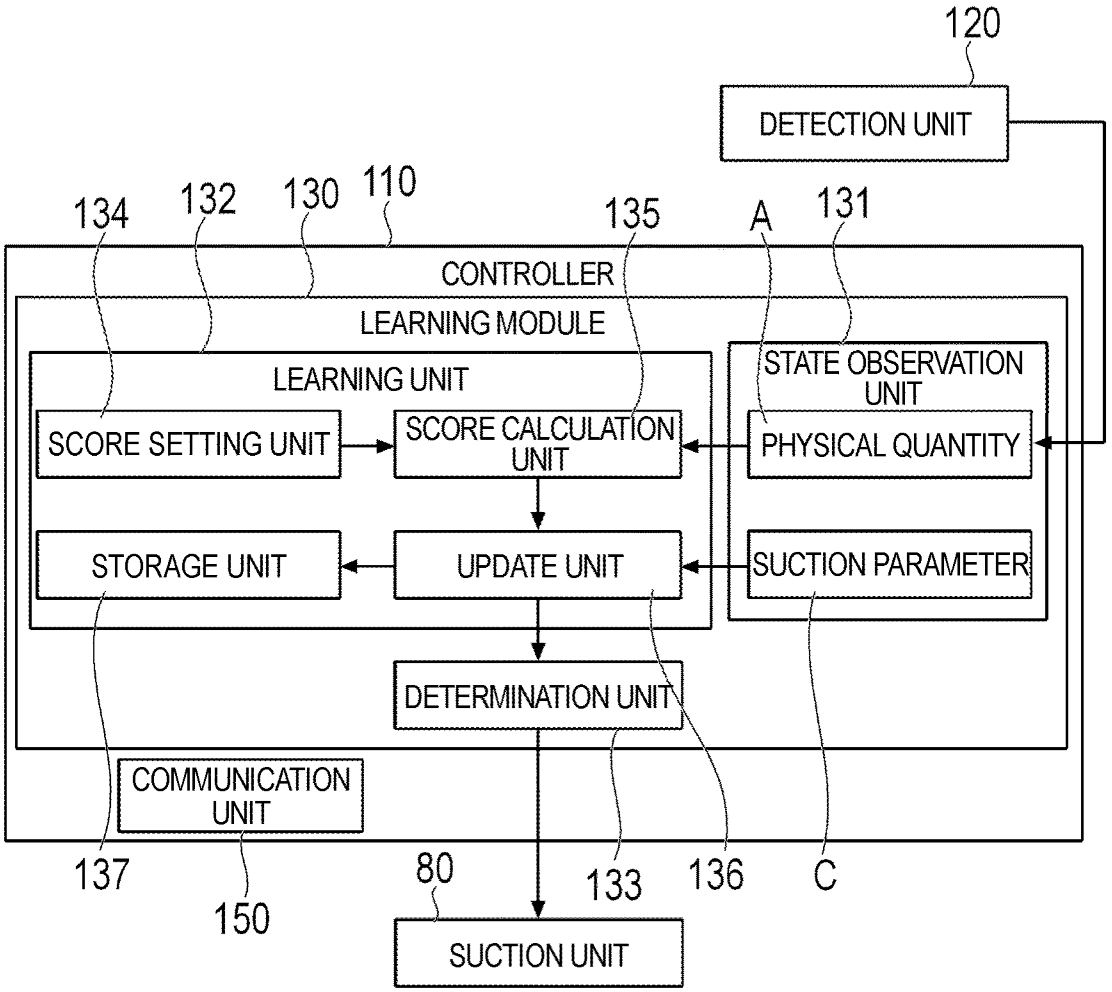
FIG. 6 is a functional block diagram of a controller of a medical system according to a second embodiment.

As illustrated in FIG. 6, a medical system 1 according to the second embodiment is different from that of the first embodiment in that the controller 110 includes a machine learning module 130 that performs machine learning.

Machine learning algorithms are generally classified into supervised learning, unsupervised learning, reinforcement learning, and the like. In the supervised learning algorithm, a set of input data and result data is given, and machine learning is performed on the basis of the set. In the unsupervised learning algorithm, only a large volume of data is given, and the machine learning is performed on the basis of the given data. The reinforcement learning algorithm changes an environment, which corresponds to the physical quantities A described above on the basis of the solution, which corresponds to the suction parameters C, output by the algorithm, and corrects the solution on the basis of a score as to how correct the output solution is. In the present embodiment, a case where reinforcement learning is performed as the machine learning will be described. Any machine learning other than the reinforcement learning may be used.

The machine learning module 130 includes a state observation unit 131, a learning unit 132, and a determination unit 133. The machine learning module 130 corresponds to an agent in reinforcement learning. The machine learning module 130 is included in the controller 110, but may be executed by, for example, an external device connectable to the medical system 1 according to the first embodiment.

The state observation unit 131 detects the state of the environment. The state observation unit 131 observes a state variable including at least one physical quantity A for cutting operation and at least one suction parameter C. The state observation unit 131 stores the physical quantity A and the suction parameter C in association with the observed time.

The learning unit 132 includes a score setting unit 134 that sets a score condition, a score calculation unit 135 that calculates a score, an update unit 136 that updates a function, and a storage unit 137 that stores a result obtained when the update unit 136 performs learning operation.

The score setting unit 134 sets a score condition. The score condition set by the score setting unit 134 is determined on the basis of, for example, the stability of the physical quantity A, the required time taken until the cutting operation is completed after the start of the cutting operation, a cutting quality, and the like. For example, the score increases in a case where the physical quantity A is determined to be stable (i.e., variation in the physical quantity A is small), and the score decreases in a case where the physical quantity A is determined not to be stable. The score decreases in a case where the required time is long, and the score increases in a case where the required cutting time is short. The score increases in a case where the cutting quality is improved, and the score decreases in a case where the cutting quality decreases. In order to perform such a determination, it is assumed that a device or software module capable of acquiring each data is provided, and an individual threshold or the like is set in advance for each data. The required time can be specified by the controller 110. The cutting quality can be calculated, for example, from an image obtained by an image detection unit (intravascular ultrasound, optical coherence tomography, imaging with a camera, ultrasonic diagnostic imaging, computed tomography, magnetic resonance imaging or the like) that can be used when the treatment target information B is acquired.

The score calculation unit 135 calculates a score on the basis of at least one physical quantity A and a score condition, which are observed by the state observation unit 131.

The update unit 136 updates a function for determining at least one suction parameter C from the current state variable on the basis of the score calculated by the score calculation unit 135. The function is, for example, an action value function.

The determination unit 133 performs learning of selection of a high-value action. The determination unit 133 determines at least one suction parameter C and an optimum correction amount of the suction parameter C from the current state variable on the basis of the learning result of the learning unit 132.

A communication unit 150 can be connected to a dedicated server via a network. Thus, the controller 110 can perform at least part of high-load arithmetic processing in the machine learning using the dedicated server via the network. Therefore, the controller 110 of the medical system 1 or the control device 2 connectable to the server performs arithmetic processing for calculating the optimal action value function or the state variable by using the server via the network, receives an arithmetic result via the network, and optimally updates the arithmetic result.

Figure 7:
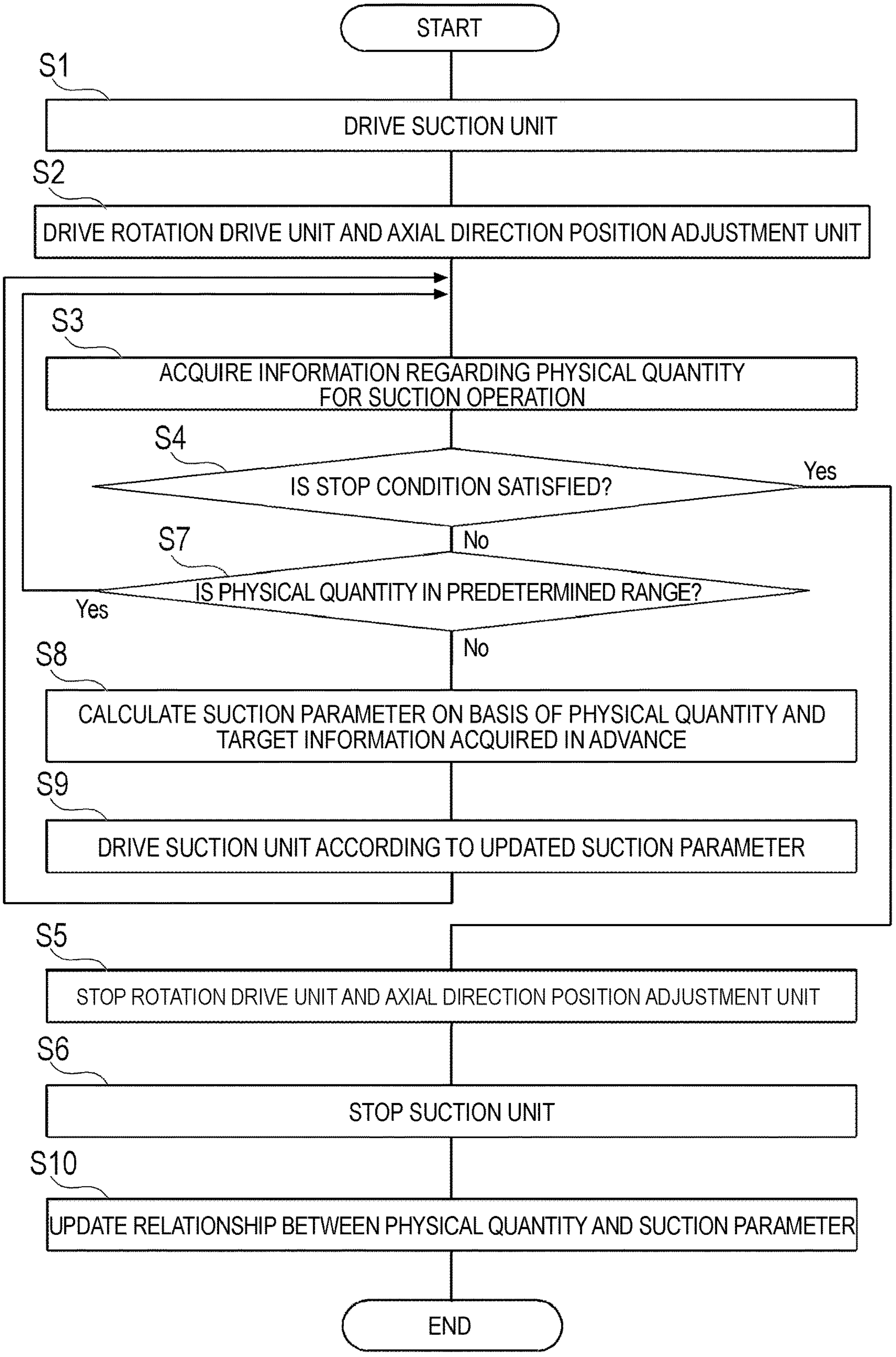
FIG. 7 is a flowchart illustrating operation of the controller according to the second embodiment.

As illustrated in FIG. 7, the processing of the machine learning module 130 is performed every time the lesion L is treated by the medical system 1 (S10). The machine learning module 130 calculates the score for each suction parameter C by the score calculation unit 135, and updates the action value function with the update unit 136 such that the score increases. The update of the action value function can be performed by, for example, a known update formula used in Q-learning. Thus, the machine learning module 130 updates at least one suction parameter C in order to cut the lesion L.

The reliability of the action value function is increased by repeatedly performing processing of the machine learning for each cutting operation. By using a highly reliable action value function, for example, at least one suction parameter C can be made more optimal such that a Q-value used in the Q-learning increases. Therefore, when the cutting operation is performed, the optimum suction parameter C can be automatically generated on the basis of the detected physical quantity A by using the action value function with increased reliability. The update of the action value function by the update unit 136 may be performed not for each procedure of cutting operation but during the procedure.

In the second embodiment, the controller 110 includes a learning unit 132 that performs learning of determining at least one suction parameter C by updating a function for determining at least one suction parameter C on the basis of a state variable having at least one physical quantity A and at least one suction parameter C. The learning unit 132 includes a score calculation unit 135 that calculates a score for a result obtained by determining at least one suction parameter C on the basis of the state variable, and an update unit 136 that updates the function on the basis of the score calculated by the score calculation unit 135, and performs learning of at least one suction parameter C for which the score is most obtained when the update unit 136 repeats the update of the function. Therefore, the medical system 1 can increase the reliability of the function for determining the suction parameter C by repeatedly performing processing of the machine learning. At least one suction parameter C can be made more optimal on the basis of a function with high reliability for determining the suction parameter C.

The present invention is not limited to the above-described embodiments, and various modifications can be made by those skilled in the art within the technical idea of the present invention. For example, the cutting unit 30 may be, for example, a structure for performing cutting operation by moving the cutting unit in the axial direction X or a member for emitting a laser beam instead of a rotating body.

What is claimed is:

1. A medical system comprising:

a device for removing an object in a body cavity, the device including:
  - a shaft portion including a rotatable drive shaft and a lumen,
  - a motor configured to rotate the drive shaft,
  - a cutter attached to a distal end of the drive shaft and configured to cut the object when the drive shaft is rotated by the motor, and
  - a pump operable according to one or more parameters to create a vacuum in the lumen to transport the cut object through the lumen;

one or more sensors each configured to detect a physical quantity related to the cut object transported through the lumen, wherein a first sensor of the sensors is configured to detect a flow rate of a liquid flowing through the lumen during a time period the vacuum is created in the lumen, and a second sensor of the sensors is configured to detect a size of a piece of the cut object that is transported through the lumen; and a controller configured to:
  - determine the parameters based on the physical quantity detected by each of the sensors, one of the parameters indicating a suction force of the vacuum created by the pump,
  - control the pump to create the vacuum in the lumen according to the determined parameters,
  - control the pump to increase the suction force in response to the flow rate detected by the first sensor falling below a threshold, and
  - after increasing the suction force, control the pump to continue to create the vacuum even when the flow rate continues to change over a predetermined time if the size detected by the second sensor exceeds a reference value.

2. The medical system according to claim 1, wherein another one of the parameters indicates the time period for creating the vacuum.

3. The medical system according to claim 1, wherein a third sensor of the sensors is configured to detect, during the time period the vacuum is created in the lumen:

an amount of negative pressure applied to the lumen, a number of pieces of the cut object that are transported through the lumen, or a hardness of a piece of the cut object that is transported through the lumen.

4. The medical system according to claim 1, wherein after increasing the suction force, the controller controls the pump to stop creating the vacuum when the flow rate continues to change over the predetermined time if the size detected by the second sensor does not exceed the reference value.

5. The medical system according to claim 1, wherein a third sensor of the sensors is configured to detect an amount of negative pressure applied to the lumen during the time period the vacuum is created in the lumen, and the controller controls the pump to increase the suction force in response to the amount of negative pressure rising above a threshold.

6. The medical system according to claim 5, wherein after increasing the suction force, the controller controls the pump to stop creating the vacuum when the amount of negative pressure continues to change over the predetermined time if the size detected by the second sensor does not exceed the reference value.

7. The medical system according to claim 5, wherein after increasing the suction force, the controller controls the pump to continue to create the vacuum even when the amount of negative pressure detected by the third sensor continues to change over the predetermined time if the size detected by the second sensor exceeds the reference value.

8. The medical system according to claim 1, wherein the controller is further configured to:

determine whether the physical quantity detected by one of the sensors is within a predetermined range, upon determining that the physical quantity is within the predetermined range, determine not to change the parameters, and upon determining that the physical quantity is not within the predetermined range, determine to change the parameters and update the parameters based on the physical quantity.

9. The medical system according to claim 1, wherein the controller is further configured to control the motor to stop before stopping the pump.

10. The medical system according to claim 1, further comprising:

another pump configured to supply a liquid into the body cavity through the shaft portion, wherein the controller is further configured to:

determine whether the physical quantity detected by one of the sensors is within a predetermined range, and upon determining that the physical quantity exceeds the predetermined range, control said another pump to supply the liquid.

11. The medical system according to claim 1, wherein the controller is further configured to perform a machine learning algorithm using a function for determining the parameters from the physical quantity, the algorithm including:

(a) determining first parameters based on a first physical quantity using the function, (b) calculating a score for the first parameters based on a second physical quantity that is detected after the pump is operated according to the first parameters, and (c) updating the function based on the calculated score, and the controller repeats steps (a)-(c) until the calculated score reaches a particular score.

12. A medical system comprising:

a device for removing an object in a body cavity, the device including:

a shaft portion including a rotatable drive shaft and a lumen, a motor configured to rotate the drive shaft, a cutter attached to a distal end of the drive shaft and configured to cut the object when the drive shaft is rotated by the motor, and a pump operable according to one or more parameters to create a vacuum in the lumen to transport the cut object through the lumen;

one or more sensors each configured to detect a physical quantity related to the cut object transported through the lumen, wherein a first sensor of the sensors is configured to detect an amount of negative pressure applied to the lumen during a time period the vacuum is created in the lumen, and a second sensor of the sensors is configured to detect a size of a piece of the cut object that is transported through the lumen; and a controller configured to:

determine the parameters based on the physical quantity detected by each of the sensors, one of the parameters indicating a suction force of the vacuum created by the pump, control the pump to create the vacuum in the lumen according to the determined parameters, control the pump to increase the suction force in response to the amount of negative pressure detected by the first sensor rising above a threshold, and after increasing the suction force, control the pump to continue to create the vacuum even when the amount of negative pressure continues to change over a predetermined time if the size detected by the second sensor exceeds a reference value.

* * * * *